United States Patent [19]

Tobutt

[11] Patent Number: Plant 6,225

[45] Date of Patent: Jul. 19, 1988

[54] COLUMNAR APPLE TREE—TUSCAN VARIETY

[75] Inventor: Kenneth R. Tobutt, Maidstone, England

[73] Assignees: The Kent Incorporated Society for Promoting Experiments in Horticulture, Maidstone; National Seed Development Organisation Limited, Cambridge, both of England

[21] Appl. No.: 852,329

[22] Filed: Apr. 15, 1986

[51] Int. Cl.[4] ..... A01H 5/03

[52] U.S. Cl. ..... Plt./34

[58] Field of Search ..... Plt./34

*Primary Examiner*—Robert E. Bagwill

*Attorney, Agent, or Firm*—Burns, Doane, Swecker & Mathis

[57] ABSTRACT

A new and distinct variety of apple tree is provided which exhibits an extremely columnar growth habit which generally resembles that of a vertical pole. The foliage is dense and compact and side branches are substantially absent. The new variety yields medium-sized asymmetric generally flat round fruit having a yellow-green skin coloration which is partially overlaid with light orange. The unique growth habit makes possible plantings of extremely high density with concomitant increased fruit yields per planting area.

1 Drawing Sheet

SUMMARY OF THE INVENTION

The new variety of apple tree was created in the course of a plant breeding program which was initiated during 1976 at the East Malling Research Station of The Kent Incorporated Society for Promoting Experiments in Horticulture at East Malling, Maidstone, Kent, England. The parents of the new variety were the Wijcik variety (U.S. Plant Pat. No. 4,382) of McIntosh apple tree, and the Greensleeves apple tree variety (non-patented in the United States). This parentage can be summarized as follows:

Wijcik × Greensleeves.

Approximately 100 crosses were made between the respective parents. Approximately 20 fruits were formed which contained five viable seeds each. Approximately 100 seedlings were formed from the germination of such seeds and the resulting trees were subjected to detailed study. A single plant of the new variety was selected. During the selection process the absence of side branches was a major factor.

It was found that the new variety of apple tree of the present invention possesses the following combination of characteristics:

(a) an erect, dense and compact growth habit which is substantially free of side branches, and
(b) the ability to form medium-sized asymmetric generally flat round fruit having a yellow-green skin coloration which is partially overlaid with light orange coloration.

The extremely columnar nature of the new variety is particularly striking. Side branches are very limited and tend to form only when the terminal bud is damaged (e.g., by mildew, etc.). When side branches occur, they can be easily removed with secateurs. The axillary buds tend to form fruit-producing spurs rather than extension shoots. The foliage is dense and compact and the internodes are short. The flowers and fruit tend to form along a single main stem or trunk which gives the entire tree the appearance of a vertical pole. The trees commonly grow in height at a rate of approximately 1.5 feet per season.

The new variety forms good quality dessert fruit having a distinctive coloration wherein a light orange coloration commonly overlays approximately 25 percent or less of a yellow-green ground coloration. The flesh of the new variety tends to be relatively soft.

The distinctive growth habit of the new variety makes possible the extremely dense planting of the new variety for commercial fruit production. For instance, the new variety can be grown in rows with the trees being spaced approximately 1 yard apart and with approximately 1 yard between rows. Accordingly, planting densities of up to approximately 5,000 unstaked trees per acre are made possible which commonly can result in increased fruit yields per planting area. The rows of trees of the new variety form sturdy natural cordons. However, in extremely windy areas it may be desirable to at least partially shelter the trees from the wind with appropriate wind barriers. Extreme wind exposure may undesirably result in the destruction of the terminal bud and thereby tend to promote secondary branching. The trees of the new variety are relatively easy to manage and require little pruning. Mechanized picking readily can be implemented. Additionally, the trees of the new variety can serve as space-saving pollinators in more conventional orchards. Such trees also can be used for ornamental purposes in gardens, parks, and along roadsides.

The new variety has been found to undergo asexual propagation by a number of routes, including budding, grafting, etc. The characteristics of the new variety have been found to be strictly transmissible by such asexual propagation from one generation to another.

The new variety performs well on dwarfing rootstocks, such as MM 106, and it is not recommended that it be grown on its own roots. Also, it has performed well at the 1984 National Fruit Trials, Brogdale Farm, Faversham, Kent, England.

Initially, the new variety was designated SA 256-24, and subsequently has been named the Tuscan variety.

BRIEF DESCRIPTION OF THE PHOTOGRAPH

The accompanying photograph shows as nearly true as it is reasonably possible to make the same, in a color illustration of this character, typical specimens of the new variety.

FIG. 1 illustrates a section of the vertical trunk of the new variety showing the abundant production of fruit having a yellow-green skin coloration partially overlaid with light orange coloration.

DETAILED DESCRIPTION

Figure 1:
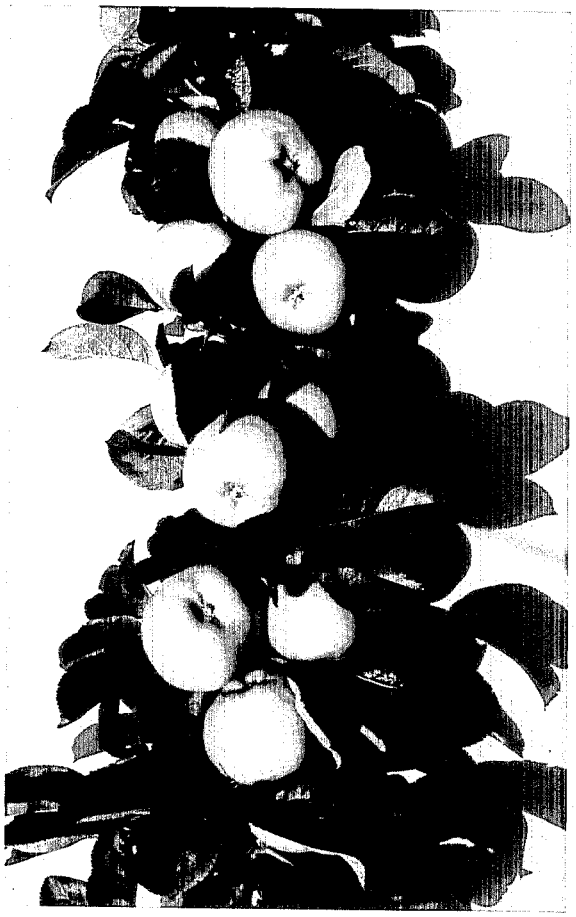

The specimens described were grown at the Brogdale Experimental Horticulture Station, Faversham, Kent, England.

Tree:

*Habit of branches.*—A conventional branching system along the tree trunk is lacking, branches rarely form when the terminal bud is undamaged.

*Growth habit.*—Compact and dense with short internodes.

*Vigor.*—Weak.

*Dormant one year old shoot.*—Pubescence is absent or very weak, medium leader thickness, and few lenticels.

Leaves:

*Leaf configuration.*—Elongated as illustrated, commonly having a length: width ratio of approximately 1.7.

*Leaf margin.*—Lightly serrate.

*Leaf appearance.*—Medium glossy.

*Petiole.*—Long, approximately 45.5 mm. in length on average.

*Leaf posture.*—Generally outwards.

Flowers:

*Dormant bud shape.*—Ovoid.

*Bud pubescence.*—Slightly more downy than the buds of the TRAJAN variety.

*Bud color.*—Red Group 58D of the R.H.S. Colour Chart.

*Flower shape.*—Flat or slightly cupped.

*Flower size.*—Medium.

*Flower color.*—Red Group 58D of the R.H.S. Colour Chart.

*Sepals.*—Predominantly green in coloration with red tips.

*Petal shape.*—Longer than broad, have a length:-breadth ratio of approximately 1.5.

*Relation of petal margins.*—Touching.

*Styles.*—Substantially the same length as the stamens, attached away from the base (i.e., approximately 3/10 of the length away from the base).

Fruit:

*Predominance of bearing.*—On spurs which are fewer and more upright than produced on the TRAJAN variety.

*Size.*—Medium, approximately 75.3 mm. on average.

*Shape.*—Generally flat and round, some oblong.

*Symmetry in sideview.*—Asymmetric.

*Ribbing.*—Present.

*Prominence of ribbing.*—Not prominent.

*Crowning at distal end.*—Present and weak.

*Aperture of eye.*—Mainly closed.

*Size of eye.*—Small.

*Length of sepal.*—Medium.

*Attitude of sepal.*—Partly reflexed.

*Spacing of sepals at base.*—Overlapping.

*Depth of basin.*—Medium, approximately 6.1 mm. on average.

*Width of basin.*—Medium, approximately 29.9 mm. on average.

*Ribbing of basin.*—Present in medium quantity.

*Protrusion of stalk.*—Moderately beyond cavity.

*Thickness of stalk.*—Medium.

*Length of stalk.*—Short, approximately 14.5 mm. on average.

*Stalk cavity depth.*—Medium, approximately 12.7 mm. on average.

*Width of stalk cavity.*—Medium, approximately 32.8 mm. on average.

*Surface texture of skin.*—Smooth.

*Bloom of skin.*—Absent.

*Greasiness of skin.*—Present in medium quantity.

*Cracking tendency of skin.*—Absent.

*Thickness of skin.*—Medium.

*Skin color.*—Ground color is yellow-green (pod green 061 with reference to the R.H.S. Horticultural Colour Chart — Page 120) and bears 25 percent or less of an attractive pale orange flush (yellow orchre 07 with reference to the R.H.S. Horticultural Colour Chart — Page 101).

*Russet.*—Sometimes present in small amounts in a buff color mainly around the basin and at times only in the cavity.

*Lenticels.*—Small in size.

*Browning of flesh.*—Medium.

*Firmness of flesh.*—Relatively soft, measures approximately 3.5 kilos on average when tested with a fruit testing penetrometer manufactured by EFFEGI, 48011, Alfonsine, Italy, using a 13 mm. head.

*Color flesh.*—Cream.

*Texture of flesh.*—Medium.

*Juiciness of flesh.*—Medium.

*Sweetness of flesh.*—Weak.

*Acidity of flesh.*—Medium.

*Flavor of flesh.*—Weak.

*Cavity beneath eye.*—U or V-shaped when examined in longitudinal section.

*Position of stamens.*—Medium when examined in longitudinal section.

*Shape of core.*—Asymmetric when examined in longitudinal section.

*Distinctness of coreline.*—Strong when examined in cross-section.

*Aperture of cells.*—Open when examined in cross-section.

*Color of fresh seed.*—Brown.

*Time of maturity for picking.*—Late.

*Time of fruit ripening for eating.*—Late.

I claim:

1. A new and distinct variety of apple tree, substantially as illustrated and described, having (a) an erect, dense and compact growth habit which is substantially free of side branches, and (b) the ability to form medium-sized asymmetric generally flat round fruit having a yellow-green skin coloration which is partially overlaid with light orange coloration.

* * * * *